(12) United States Patent
Sekura et al.

(10) Patent No.: US 9,095,563 B2
(45) Date of Patent: Aug. 4, 2015

(54) **TOPICAL TREATMENTS INCORPORATING *CANNABIS* SP. DERIVED BOTANICAL DRUG PRODUCT**

(71) Applicants: Ronald D. Sekura, Key Largo, FL (US); Roscoe M. Moore, Jr., Rockville, MD (US)

(72) Inventors: Ronald D. Sekura, Key Largo, FL (US); Roscoe M. Moore, Jr., Rockville, MD (US)

( * ) Notice: Subject to any disclaimer, the term of this patent is extended or adjusted under 35 U.S.C. 154(b) by 0 days.

(21) Appl. No.: 14/498,555

(22) Filed: Sep. 26, 2014

(65) Prior Publication Data

US 2015/0086494 A1 Mar. 26, 2015

Related U.S. Application Data

(60) Provisional application No. 61/882,990, filed on Sep. 26, 2013.

(51) Int. Cl.
| | |
|---|---|
| *A01N 65/00* | (2009.01) |
| *A61K 31/352* | (2006.01) |
| *A61K 31/573* | (2006.01) |
| *A61K 31/085* | (2006.01) |
| *A61K 31/245* | (2006.01) |
| *A61K 31/047* | (2006.01) |
| *A61K 31/235* | (2006.01) |
| *A61K 31/045* | (2006.01) |
| *A61K 36/185* | (2006.01) |
| *A61K 36/61* | (2006.01) |
| *A61K 36/00* | (2006.01) |

(52) U.S. Cl.
CPC ............ *A61K 31/352* (2013.01); *A61K 31/045* (2013.01); *A61K 31/047* (2013.01); *A61K 31/085* (2013.01); *A61K 31/235* (2013.01); *A61K 31/245* (2013.01); *A61K 31/573* (2013.01); *A61K 36/00* (2013.01); *A61K 36/185* (2013.01); *A61K 36/61* (2013.01)

(58) Field of Classification Search
CPC ..................................................... A61K 36/00
USPC .......................................................... 424/725
See application file for complete search history.

(56) References Cited

U.S. PATENT DOCUMENTS

| | | | |
|---|---|---|---|
| 6,630,507 | B1 | 10/2003 | Hampson et al. |
| 7,026,360 | B1 | 4/2006 | Festo |
| 2008/0206161 | A1 | 8/2008 | Tamarkin et al. |
| 2008/0255224 | A1 | 10/2008 | Blum |

OTHER PUBLICATIONS

International Search Report and Written Opinion issued Dec. 29, 2014 in PCT/US2014/057801.

*Primary Examiner* — Michael Meller
(74) *Attorney, Agent, or Firm* — Oblon, McClelland, Maier & Neustadt, L.L.P.

(57) ABSTRACT

A topical formulation comprising a *Cannabis* derived botanical drug product, wherein the concentration of tetrahydrocannabinol, cannabidiol, or both in the topical formulation is greater than 2 milligrams per kilogram.

30 Claims, 1 Drawing Sheet

TOPICAL TREATMENTS INCORPORATING *CANNABIS* SP. DERIVED BOTANICAL DRUG PRODUCT

CROSS-REFERENCE TO RELATED APPLICATIONS

This application claims the benefit of U.S. Provisional Application No. 61/882,990, filed on Sep. 26, 2013, which is herein incorporated by reference in its entirety.

FIELD OF THE INVENTION

This invention relates to topical formulations that comprise a *Cannabis* derived botanical drug product, methods of making the topical formulations, and methods of using the topical formulations in treating dermatological diseases.

BACKGROUND OF THE INVENTION

The botanical genus *Cannabis* includes the species *indica* and *sativia*. Within these species multiple distinct varieties and strains have been and continue to be developed. The genus known produce more than 480 different chemical substances. Among these chemicals approximately 80 distinct entities exist which are classified as cannabinoids. The two species differ in the amount of tetrahydrocannabinol (THC) produced. *Cannabis sativia* produces higher levels of THC. The psychotropic affects associated with THC have made the *sativia* species preferred as a recreational substance and for medicinal use where the psychotropic effect is desired. Notwith-standing THC and other chemical entities produced by the *sativia* species have significant and diverse pharmacological action.

The *indica* species is cultivable in cooler climates and produce more cannabidiol (CBD) than THC. This allows production of extracts with low THC. The seeds from *Cannabis* species are used to produce hemp oil which is used industrially and also as a nutritional supplement.

*Cannabis* derived materials which may contain THC and CBD in addition to numerous natural substances produced by the plants have been reported to have diverse pharmacological activities that include analgesic, anti-inflammatory, anti-cancer, antibiotic, and anti-oxidant activity.

In most jurisdictions throughout the world, including the United States, cannabinoids (which include THC, structurally related compounds, and in some instances CBD) are controlled substances and use for medical purposes has been discouraged. Since some products derived from *cannabis* species are economically important (e.g. hemp oil) maximum levels for cannabinoids in products have been set. In Canadian hemp seed oil THC levels are usually below detection limit of 4 ppm (parts per million, or 4 mg/kg). Legal limit for THC content in foodstuffs in Canada is 10 ppm. Some European countries have limits of 5 ppm or none-detected, some EU countries do not have such limits at all.

Relaxation of laws limiting the use of marijuana and thus cannabinoid containing products, in some jurisdictions (e.g. as of 2013 medical marijuana is considered legal in 20 states and the District of Columbia) has opened the door to encourage development of new cannabinoid containing products. To a large extent major focus has been directed at systemically administered formulations and formulations taking advantage of psychotropic activities or use of cannabinoids as anti-oxidants and neuroprotectants.

U.S. Pat. No. 6,630,507, incorporated herein by reference, discloses pharmaceutical compounds and compositions that are useful as tissue protectants, such as neuroprotectants and cardioprotectants. The compounds and compositions are disclosed to be used in the treatment of acute ischemic neurological insults or chronic neurodegenerative diseases. The disclosed compositions include cannabidiol and other cannabinoids, and the compositions are disclosed to include THC in amounts that do not promote psychoactive or psychotoxic effects. Accordingly, there is no disclosure of topical compositions that include THC in amounts that exceed the detection limit of THC.

In view of the foregoing, there is a need for topical formulations that comprise a *Cannabis* derived botanical drug product that take advantage of diverse pharmacologic activities, that are beyond and unforeseen from those described in U.S. Pat. No. 6,630,507 B1, in treatment of dermatologic and other diseases. We also define that the major cannabinoids are present in our products at concentrations exceeding the commonly applied maximum levels that define *cannabis* derived products, such as hemp oil, legal for non-drug use can provide unexpected and highly beneficial treatments for a wide variety of diseases.

BRIEF SUMMARY OF THE INVENTION

One object of the invention is to provide a topical preparation comprising a *Cannabis* derived botanical drug product such that the concentration of tetrahydrocannabinol in the final product is greater than 2 milligrams per kilogram. Other objects of the invention include methods of making the topical preparations and methods of using the topical preparations to treat dermatological diseases.

EMBODIMENTS OF THE PRESENT INVENTION

Figure 1:
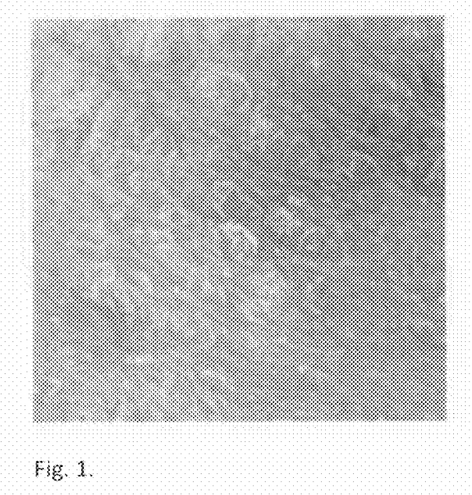
FIG. 1 shows an area of skin affected by plaque psoriasis.
Figure 2:
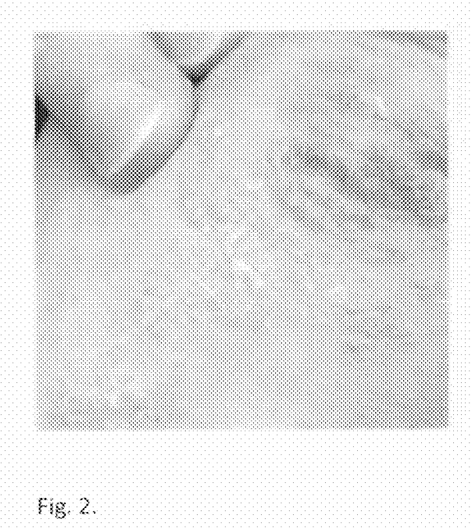
FIG. 2 shows the results of treating psoriasis affected area by application of topical formulation comprising a *Cannabis* derived botanical drug product according to the present invention.

One embodiment of the present invention is [1] a topical formulation comprising a *Cannabis* derived botanical drug product, wherein the concentration of tetrahydrocannabinol in the topical formulation is greater than 2 milligrams per kilogram.

Another embodiment of the present invention is [2] a topical formulation comprising a *Cannabis* derived botanical drug product, wherein the concentration of cannabidiol in the topical formulation is greater than 2 milligrams per kilogram.

Another embodiment of the present invention is [3] a topical formulation comprising a *Cannabis* derived botanical drug product, wherein the concentration of each, cannabidiol and tetrahydrocannabinol, in the topical formulation is greater than 2 milligrams per kilogram.

Another embodiment of the present invention is [4] a topical formulation according to [1], [2], or [3], which further comprises hydrocortisone or any steroid within Groups I to VII in the US classification system in a therapeutically effective amount.

Another embodiment of the present invention is [5] a topical formulation according to [1], [2], or [3], which further comprises an antibiotic compound in a therapeutically effective amount.

Another embodiment of the present invention is [6] a topical formulation according to [1], [2], or [3], which further comprises an antiseptic compound in a therapeutically effective amount.

Another embodiment of the present invention is [7] a topical formulation according to [1], [2], or [3], which further comprises an antifungal compound in a therapeutically effective amount.

Another embodiment of the present invention is [8] a topical formulation according to [1], [2], or [3], which further comprises an anti-acne agent in a therapeutically effective amount.

Another embodiment of the present invention is [9] a topical formulation according to [1], [2], or [3], which further comprises a soothing, smoothing, moisturizing or protective agent in a therapeutically effective amount.

Another embodiment of the present invention is [10] a topical formulation according to [1], [2], or [3], which further comprises a UV-absorbing compound in a therapeutically effective amount.

Another embodiment of the present invention is [11] a topical formulation according to [1], [2], or [3], which further comprises an analgesic compound in a therapeutically effective amount.

Another embodiment of the present invention is [12] a topical formulation according to [1], [2], or [3], which further comprises an anti-viral compound in a therapeutically effective amount.

Another embodiment of the present invention is [13] a topical formulation according to [1], [2], or [3], which is in the form of a lotion.

Another embodiment of the present invention is [14] a topical formulation according to [1], [2], or [3], which is in the form of a cream.

Another embodiment of the present invention is [15] a topical formulation according to [1], [2], or [3], which is in the form of a salve.

Another embodiment of the present invention is [16] a topical formulation according to [1], [2], or [3], which is in the form of a liniment.

Another embodiment of the present invention is [17] a topical formulation according to [1], [2], or [3], which is in the form of an ointment.

Another embodiment of the present invention is [18] a topical formulation according to [1], [2], or [3], which is in the form of a gel.

Another embodiment of the present invention is [19] a topical formulation according to [1], [2], or [3], which is in the form of a paste.

Another embodiment of the present invention is [20] a topical formulation according to [1], [2], or [3], which is in the form of a tonic.

Another embodiment of the present invention is [21] a topical formulation according to [1], [2], or [3], which is in the form of an unguent.

Another embodiment of the present invention is [22] a topical formulation according to [1], [2], or [3], which is in the form of a nasal spray.

Another embodiment of the present invention is [23] a topical formulation according to [1], [2], or [3], which is in the form of a soap.

Another embodiment of the present invention is [24] a topical formulation according to [1], [2], or [3], which is in the form of a shampoo.

Another embodiment of the present invention is [25] a topical formulation according to [1], [2], or [3], which is in the form of a lip balm.

DETAILED DESCRIPTION OF THE INVENTION

Unless indicated otherwise, the indefinite articles "a" and "an" are synonymous with "at least one" or "one or more." Unless indicated otherwise, definite articles used herein, such as "the," also include the plural of the noun. Terms used herein such as "comprising," "consisting essentially of," and "consisting of" have their ordinary and customary meaning under U.S. patent law. Unless otherwise indicated, the transitional term "comprising" is synonymous with "including," "containing," or "characterized by" and is inclusive or open-ended and does not exclude additional, unrecited elements or method stages. Unless otherwise indicated, the transitional term "consisting essentially of" limits the scope of the claim to the materials specified and/or recited in the body of the claim or method stages specified and/or recited in the body of the claim, and this transitional phrase excludes those materials or stages that materially affect the basic and novel characteristics of the claimed invention. Unless otherwise indicated, the transitional term "consisting of" limits the scope of the claim to only those materials specified and/or recited in the body of the claim or to only those method stages specified and/or recited in the body of the claim.

The units for the concentration of compounds in topical formulations as used herein are typically represented as milligrams per kilogram, unless otherwise indicated. Milligrams per kilogram is equal to parts per million ("ppm").

Unless otherwise indicated, the term "*Cannabis*" used herein refers to at least one of *Cannabis sativia* and *Cannabis indica*. Some of the materials which are produced by the *Cannabis* species have been shown to have pharmacologic activity. Such materials are discussed in turn.

Tetrahydrocannabinol, which is abbreviated herein as "THC" unless otherwise indicated, is the principal psychoactive constituent (or cannabinoid) of the *cannabis* plant. THC is also known as delta-9-tetrahydrocannabinol (Δ9-THC). THC was first isolated in 1964, and, in its pure form, it is a glassy solid when cold and becomes viscous and sticky if warmed. Pharmaceutical formulations that comprise THC, known by its INN dronabinol, are available by prescription in the U.S. and Canada under the brand name MARINOL. THC is an aromatic terpenoid, and it has a very low solubility in water but good solubility in most organic solvents, specifically lipids and alcohols. THC also exhibits high UV-B (280-315 nm) absorbance.

Cannabidiol (CBD) is one of at least 85 cannabinoids found in *cannabis*. It is a major constituent of the plant, second to THC, and represents up to 40% in its extracts. Compared with THC, cannabidiol is non-psychoactive, and is considered to have a wider scope of medical applications than THC, including to epilepsy, multiple sclerosis spasms, anxiety disorders, schizophrenia, nausea, convulsion and inflammation, as well as inhibiting cancer cell growth. CBD may decrease the rate of THC clearance from the body, perhaps by interfering with the metabolism of THC in the liver. CBD has displayed sedative effects in animal tests, while other studies have found that CBD may increases alertness. CBD has been shown to reduce growth of aggressive human breast cancer cells in vitro, and to reduce their invasiveness.

CBD is an anti-oxidant, has anti-inflammatory activity and analgesic properties in animal studies. It has been shown to inhibit the growth of bacteria, and is thought to exhibit psychoactive properties that are distinct from THC that include anticonvulsant and anti-epileptic properties.

Other pharmacological cannabinoid activities include β-sitosterol, tocopherols, terpenes, methyl salicylate, hemp oil or hempseed oil, hash oil, and hashish. These are discussed in turn.

Beta-Sitosterol: Although studies have primarily demonstrated the efficacy of β-sitosterol in reducing hypercholesterolemia, additional antiviral, antifungal, and anti-inflammatory properties have been studied and observed.

Tocopherols: Antioxidant properties of alpha and gama tocopherols have been known and exploited for some time.

Terpenes: pharmacological properties of β-caryophyllene would include anti-inflammatory and cytoprotective activities which may too be active in the seed oil.

Methyl salicylate: a compound that exhibits antipyretic, anti-inflammatory and analgesic properties.

Hemp oil or hempseed oil is obtained by pressing hemp seeds. Cold pressed, unrefined hemp oil is dark to clear light green in color, with a pleasant nutty flavor. The darker the color, the grassier the flavor. While most hemp oil is produced from strains of Cannabis sativia that produce low levels of THC, we can include in some of our formulations hemp oil from strains of Cannabis indica.

Refined hempseed oil is clear and colorless, with little flavor and lacks natural vitamins and antioxidants. Refined hempseed oil is primarily used in body care products. Industrial hempseed oil is used in lubricants, paints, inks, fuel, and plastics. Hempseed oil has found some limited use in the production of soaps, shampoos and detergents. The oil is of high nutritional value because of its 3:1 ratio of omega-6 to omega-3 essential fatty acids, which matches the balance required by the human body. It has also received attention in recent years as a possible feedstock for the large-scale production of biodiesel. There are a number of organizations that promote the production and use of hempseed oil.

Hempseed oil is generally manufactured from varieties of Cannabis sativa that do not contain significant amounts of THC, the psychoactive element present in the cannabis plant. This manufacturing process typically includes cleaning the seed to 99.99% before pressing the oil. There is no THC within the hempseed, although trace amounts of THC may be found in hempseed oil when plant matter adheres to the seed surface during manufacturing. The modern production of hempseed oil, particularly in Canada, has successfully lowered THC values since 1998. Regular accredited sampling of THC in Canadian hemp seed oil shows THC levels usually below detection limit of 4 ppm (parts per million, or 4 mg/kg). Legal limit for THC content in foodstuffs in Canada is 10 ppm. Some European countries have limits of 5 ppm or none-detected, some EU countries do not have such limits at all. For some products production of hemp oil from Cannabis species and strains that produce THC is desirable. Hemp oil is of high nutritional value because of its 3:1 ratio of omega-6 to omega-3 essential fatty acids, About 30-35% of the weight of hempseed is an edible oil that contains about 80% as essential fatty acids (EFAs); i.e., linoleic acid, omega-6 (LA, 55%), α-linolenic acid, omega-3 (ALA, 22%), in addition to γ-linolenic acid, omega-6 (GLA, 1-4%) and stearidonic acid, omega-3 (SDA, 0-2%). The proportions of linoleic acid and α-linolenic acid in one tablespoon per day (15 ml) of hempseed oil easily provide human daily requirements for EFAs. Unlike flaxseed oil, hempseed oil can be used continuously without developing a deficiency or other imbalance of EFAs. This has been demonstrated in a clinical study, where the daily ingestion of flaxseed oil decreased the endogenous production of GLA.

Hash oil, not to be confused with hempseed oil, is used for both medicinal and recreational purposes and made from the mature female flowers and leaves of the drug cannabis, thus having a much higher THC content. Hash oil should not be confused with hemp, as the modern usage of the word 'hemp' is reserved for plants that meet the legal requirement of containing 0.3% THC or less.

Hash oil (also known as honey oil, dabs, shatter, or earwax) is a resinous matrix of cannabinoids obtained from the cannabis plant by solvent extraction. Hash oil is the most potent of three main cannabis products, which are herb (marijuana), resin (hashish), and oil (hash oil).

Reported THC contents vary between sources. The 2009 World Drug Reports reports THC content as "may exceed 60%". A 2013 American forensic science book gave a range of 10-30% delta-9 THC by weight. A 1972 American forensic journal reported a range of 20-65%.

Hash oil is a cannabis product obtained from separating resins from leaves by solvent extraction. Cannabis is boiled in a solvent to form a viscous liquid which is then strained and the solvent is evaporated to yield hash oil. Flammable solvents used in extraction makes the process dangerous. Newer methods like $CO_2$ extraction provide a safer way to extract the resin. $CO_2$ extraction is a method of using high pressure to force a solvent through plant matter. The solvent used for extraction is carbon dioxide. The solvent is pushed through the plant matter at a high pressure and separates the cannabinoid resins and terpenes from the plant matter. The result is pure, transparent, amber oil. Carbon dioxide is a natural product which leaves behind no residues. The purity of $CO_2$ is its biggest advantage over all other solvents used for plant extraction. Currently, a popular extraction solvent is butane which can potentially leave heavy metals behind in the extracted product.

Hashish, often known as "hash", is a cannabis product composed of compressed or purified preparations of stalked resin glands, called trichomes, collected from the unfertilized buds of the cannabis plant. It contains the same active ingredients—such as THC and other cannabinoids—but in higher concentrations than unsifted buds or leaves.

Hashish may be solid or resinous depending on the preparation; pressed hashish is usually solid, whereas water-purified hashish—often called "bubble melt hash"—is often a paste-like substance with varying hardness and pliability, its color most commonly light to dark brown but varying toward green, yellow, black or red. [citation needed] It is consumed by being heated in a pipe, hookah, bong, bubbler, vaporizer, hot knife (placed between the tips of two heated knife blades), smoked in joints, mixed with cannabis buds or tobacco (the latter being more common in Europe, South America as Brazil and Africa), or cooked in foods. Hashish use as a medicine and recreational drug dates back to at least the 3rd millennium BC.

With a view to the foregoing, the present inventors have formulated compositions that comprise a Cannabis derived botanical drug product. The US Food and Drug Administration has defined Botanical Drug Product as follows:

A botanical drug product consists of vegetable materials, which may include plant materials, algae, macroscopic fungi, or combinations thereof; or A botanical drug product may be available as (but not limited to) a solution (e.g., tea), powder, tablet, capsule, elixir, topical, or injection.

Botanical drug products often have unique features, for example, complex mixtures, lack of a distinct active ingredient, and substantial prior human use. Fermentation products and highly purified or chemically modified botanical substances are not considered botanical drug products.

As used herein and unless otherwise indicated, the term "*Cannabis* derived biological drug product" is prepared form varieties of *Cannabis indica* and *sativia*, which include oils pressed from the seeds; powders prepared for various plant parts including flowers, leaves, stems, buds, and trichomes; extracts prepared from the various parts including flowers, leaves, stems, buds, and trichomes, which includes extracts prepared using organic solvents, water extraction, alcohol extracts, and liquid carbon dioxide extracts; hemp oil; hashish oil; hashish; and fractions of extracts or oils prepared by chromatography, phase partition, temperature fractionation, distillation or other methods employed for fractionation.

Most preferably, the term "a *Cannabis* derived botanical drug product" refers to the compounds obtained from chemical extraction of *Cannabis*, provided that at least one of THC and CBD is present in the *Cannabis* derived botanical drug product.

One embodiment of the present invention is a topical formulation comprising a *Cannabis* derived botanical drug product, wherein the concentration of tetrahydrocannabinol in the topical formulation is greater than 2 milligrams per kilogram.

Another embodiment of the present invention is a topical formulation comprising a *Cannabis* derived botanical drug product, wherein the concentration of cannabidiol in the topical formulation is greater than 2 milligrams per kilogram.

Another embodiment of the present invention is a topical formulation comprising a *Cannabis* derived botanical drug product, wherein the concentration of each, cannabidiol and tetrahydrocannabinol, in the topical formulation is greater than 2 milligrams per kilogram.

Preferably, the amount of tetrahydrocannabinol in the topical formulation according to the present invention is from 2 to 100 milligrams per kilogram, more preferably from 2 to 50 milligrams per kilogram, and more preferably from 2 to 25 milligrams per kilogram. The most preferred amount of tetrahydrocannabinol in the topical formulation according to the present invention is from 2 to 10 milligrams per kilogram. All rational numbers between the preceding minima and maxima are included in the ranges.

Preferably, the amount of cannabidiol in the topical formulation according to the present invention is from 2 to 100 milligrams per kilogram, more preferably from 2 to 50 milligrams per kilogram, and more preferably from 2 to 25 milligrams per kilogram. The most preferred amount of cannabidiol in the topical formulation according to the present invention is from 2 to 10 milligrams per kilogram. All rational numbers between the preceding minima and maxima are included in the ranges.

Preferably, the amount of each of tetrahydrocannabinol and cannabidiol, independently, in the topical formulation according to the present invention is from 2 to 100 milligrams per kilogram, more preferably from 2 to 50 milligrams per kilogram, and more preferably from 2 to 25 milligrams per kilogram. The most preferred amount of each of tetrahydrocannabinol and cannabidiol, independently, in the topical formulation according to the present invention is from 2 to 10 milligrams per kilogram. All rational numbers between the preceding minima and maxima are included in the ranges.

In some embodiments of the present invention, the topical formulation further comprises hydrocortisone or any steroid within Groups I to VII in the US classification system. Group I steroids include, but are not limited to, clobetasol propionate, betamethasone dipropionate, halobetasol, and diflorasone diacetate. Group II steroids include, but are not limited to, fluocinonide, halcinonide, amcinonide, and desoximetasone. Group III steroids include, but are not limited to, triamcinolone acetonide, mometasone furoate, fluticasone propionate, betamethasone dipropionate, and halometasone. Group IV steroids include, but are not limited to, fluocinolone acetonide, hydrocortisone valerate, hydrocortisone butyrate, flurandrenolide, triamcinolone acetonide, and mometasone furoate. Group V steroids include, but are not limited to, fluticasone propionate, desonide, fluocinolone acetonide, and hydrocortisone valerate. Group VI steroids include, but are not limited to, alclometasone dipropionate, triamcinolone acetonide, fluocinolone acetonide, and desonide. Group VII steroids include, but are not limited to, hydrocortisone (2.5%) and hydrocortisone (1%). The amount of hydrocortisone or steroid within Groups I to VII in the topical formulation is not particularly limited, so long as it is a therapeutically effective amount. A preferred amount is from 0.01 to 5 wt %, relative to the total amount of the topical formulation, more preferably from 0.1 to 1 wt %, relative to the total amount of the topical formulation.

In some embodiments of the present invention, the topical formulation further comprises an antibiotic compound. The antibiotic compound is not particularly limited, and is preferably at least one member selected from the group consisting of ampicillin, bacampicillin, carbenicillin indanyl, mezlocillin, piperacillin, ticarcillin, amoxicillin-clavulanic acid, ampicillin-sulbactam, benzylpenicillin, cloxacillin, dicloxacillin, methicillin, oxacillin, penicillin G, penicillin V, piperacillin tazobactam, ticarcillin clavulanic acid, nafcillin, procaine penicillin, cefadroxil, cefazolin, cephalexin, cephalothin, cephapirin, cephradine, cefaclor, cefamandol, cefonicid, cefotetan, cefoxitin, cefprozil, ceftmetazole, cefuroxime, loracarbef cefdinir, ceftibuten, cefoperazone, cefixime, cefotaxime, cefpodoxime proxetil, ceftazidime, ceftizoxime, ceftriaxone, cefepime, azithromycin, clarithromycin, clindamycin, dirithromycin, erythromycin, lincomycin, troleandomycin, cinoxacin, ciprofloxacin, enoxacin, gatifloxacin, grepafloxacin, levofloxacin, lomefloxacin, moxifloxacin, nalidixic acid, norfloxacin, ofloxacin, sparfloxacin, trovafloxacin, oxolinic acid, gemifloxacin, perfloxacin, imipenem-cilastatin, meropenem, and aztreonam. The amount of the antibiotic compound in the topical formulation is not particularly limited, so long as it is a therapeutically effective amount. A preferred amount is from 0.01 to 5 wt %, relative to the total amount of the topical formulation, more preferably from 0.1 to 1 wt %, relative to the total amount of the topical formulation.

In some embodiments of the present invention, the topical formulation further comprises an antiseptic compound. The antiseptic compound is not particularly limited, and is preferably at least one member selected from the group consisting of iodine, manuka honey, octenidine dihydrochloride, phenol, polyhexanide, sodium chloride, sodium hypochlorite, calcium hypochlorite, sodium bicarbonate, methyl paraben, and sodium dehydroacetate. The amount of the antiseptic compound in the topical formulation is not particularly limited, so long as it is a therapeutically effective amount. A preferred amount is from 0.01 to 5 wt %, relative to the total amount of the topical formulation, more preferably from 0.1 to 1 wt %, relative to the total amount of the topical formulation.

In some embodiments of the present invention, the topical formulation further comprises an antifungal agent. The antifungal agent is not particularly limited, and is preferably at least one member selected from the group consisting of amphotericin B, candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, fluconazole, isavuconazole, itraconazole, posaconazole, ravuconazole, terconazole, voriconazole, abafungin, amorolfin, butenafine, naftifine, terbinafine, anidulafungin, caspofungin, micafungin, benzoic acid, ciclopirox, flucytosine, griseofulvin, haloprogin, tolnaftate, undecylenic acid, crystal violet, and balsam of Peru. The amount of the antifungal agent in the topical formulation is not particularly limited, so long as it is a therapeutically effective amount. A preferred amount is from 0.01 to 5 wt %, relative to the total amount of the topical formulation, more preferably from 0.1 to 1 wt %, relative to the total amount of the topical formulation.

In some embodiments of the present invention, the topical formulation further comprises an anti-acne compound. The anti-acne agent is not particularly limited, and is preferably at least one member selected from the group consisting of salicylic acid and benzoyl peroxide. The amount of the anti-acne compound in the topical formulation is not particularly limited, so long as it is a therapeutically effective amount. A preferred amount is from 0.01 to 5 wt %, relative to the total amount of the topical formulation, more preferably from 0.1 to 1 wt %, relative to the total amount of the topical formulation.

In some embodiments of the present invention, the topical formulation further comprises a humectant, which can be referred to as a soothing, smoothing, moisturizing or protective agent. The humectant is not particularly limited, and is preferably at least one member selected from the group consisting of calamine, dodecylsulphate, sodium lauryl sulphate (SLS), a polyoxyethylene ester of polysorbitan, such as monooleate, monolaurate, monopalmitate, monostearate esters, esters of sorbitan, the polyoxyethylenes ethers, the sodium dioctylsulphosuccinate (DOSS), lecithin, and sodium docusate. Sodium lauryl sulphate and calamine are the most preferred humectants. The amount of the humectant in the topical formulation is not particularly limited, so long as it is a therapeutically effective amount. A preferred amount is from 0.01 to 5 wt %, relative to the total amount of the topical formulation, more preferably from 0.1 to 1 wt %, relative to the total amount of the topical formulation.

In some embodiments of the present invention, the topical formulation further comprises a UV-absorbing compound, which can be referred to as a sunscreen agent. The UV-absorbing compound is not particularly limited, and is preferably at least one member selected from the group consisting of glyceryl PABA, padimate O, roxadimate, dioxybenzone, oxybenzone, sulisonbenzone, octocrylene, octyl methoxycinnamate, ethoxyethyl p-methoxycinnamate, homomenthyl salicylate, ethylhexyl salicylate, trolamine salicylate, avobenzone, ecamsule, ensulizole, bemotrizinol, and bisoctrizole. The amount of the UV-absorbing compound in the topical formulation is not particularly limited, so long as it is a therapeutically effective amount. A preferred amount is from 0.01 to 5 wt %, relative to the total amount of the topical formulation, more preferably from 0.1 to 1 wt %, relative to the total amount of the topical formulation.

In some embodiments of the present invention, the topical formulation further comprises an analgesic agent. The analgesic agent is not particularly limited, and is preferably at least one member selected from the group consisting of methyl salicylate, codeine, morphine, methadone, pethidine, buprenorphine, hydromorphine, levorphanol, oxycodone, fentanyl, and a non-steroidal anti-inflammatory drug. The amount of the analgesic agent in the topical formulation is not particularly limited, so long as it is a therapeutically effective amount. A preferred amount is from 0.01 to 5 wt %, relative to the total amount of the topical formulation, more preferably from 0.1 to 1 wt %, relative to the total amount of the topical formulation.

In some embodiments of the present invention, the topical formulation further comprises an anti-viral compound. The anti-viral compound is not particularly limited, and is preferably at least one member selected from the group consisting of acyclovir, famciclovir, penciclovir, valacyclovir, trifluridine, docosanol, amantadine, rimantadine, oseltamivir, and zanamivir. The amount of the anti-viral compound in the topical formulation is not particularly limited, so long as it is a therapeutically effective amount. A preferred amount is from 0.01 to 5 wt %, relative to the total amount of the topical formulation, more preferably from 0.1 to 1 wt %, relative to the total amount of the topical formulation.

The form of the topical formulations of the present invention is not particularly limited, provided that it is in a form that promotes its use as a topical formulation. Non-limiting examples of the form include a lotion, a cream, a salve, a liniment, an ointment, a gel, a paste, a tonic, an unguent, a nasal spray, a soap, a shampoo, and a lip balm.

Unless otherwise indicated, the term "cream" as used herein relates to an emulsion of oil and water in approximately equal proportions, which penetrates stratum corneum outer layer of skin well. Creams are usually topical preparations for application to the skin. Creams for application to mucus membranes such as those of the rectum or vagina are also used. Creams may be considered pharmaceutical products as even cosmetic creams are based on techniques developed by pharmacy and unmedicated creams are highly used in a variety of skin conditions (dermatoses). The use of the finger-tip unit concept may be helpful in guiding how much topical cream is required to cover different areas. Creams are usually semi-solid emulsions that are mixtures of oil and water. They are divided into two types: oil-in-water (O/W) creams, which are composed of small droplets of oil dispersed in a continuous phase; and water-in-oil (W/O) creams, which are composed of small droplets of water dispersed in a continuous oily phase. Oil-in-water creams are more comfortable and cosmetically acceptable as they are less greasy and more easily washed off using water. Water-in-oil creams are more difficult to handle but many drugs which are incorporated into creams are hydrophobic and will be released more readily from a water-in-oil cream than an oil-in-water cream. Water-in-oil creams are also more moisturizing as they provide an oily barrier which reduces water loss from the stratum corneum, the outermost layer of the skin.

Creams can provide a barrier to protect the skin. This may be a physical barrier or a chemical barrier as with UV-absorbing compounds. To aid in the retention of moisture (especially water-in-oil creams), creams are usually used for a variety of purposes including cleansing, emollient effects, and as a vehicle for drug substances such as local anesthetics, anti-inflammatories (NSAIDs or corticosteroids), hormones, antibiotics, antifungals or counter-irritants, and *cannabis* derived botanical drug product.

Liniments usually refer to topical formulations for application to the skin. Preparations of this type are also called balm. Liniments are of a similar viscosity to lotions (being significantly less viscous than an ointment or cream) but unlike a lotion a liniment is applied with friction; that is, a liniment is always rubbed into the skin. Liniments are typically sold to relieve pain and stiffness, such as from sore muscles or from arthritis. These liniments typically are formulated from alcohol, acetone, or similar quickly evaporating solvents and usually comprise counterirritant aromatic chemical compounds such as methyl salicilate, benzoin resin, or capsaicin. Liniments are a common substance used by trainers and owners of horses. They may be applied diluted or full-strength, usually added into a bucket of water when sponged on the body. Liniments are especially useful in hot weather to help a hot horse cool down: the alcohols help the product to quickly evaporate, and the oils they contain cause the capillaries in the skin to dilate, also increasing the cooling process.

Unless otherwise indicated, the term "ointment" relates to compositions where oil and water are present in a ratio of from 7:1 to 2:1, preferably, from 5:1 to 3:1, most preferably about 4 parts to one. Ointments provide barrier against moisture loss. Usually, ointments are formulations using oils, waxes, water, alcohols, petroleum products, water, and other agents to prepare formulations with various viscosities and solvent properties. Commonly used formulations include oleaginous base (White Ointment), absorption base, W/O emulsion base (Cold Cream type base), O/W emulsion base (Hydrophilic Ointment), water soluble base, in addition to others. These preparations are used to dissolve or suspend substances or products with medicinal or cosmetic value. These formulations are suited for incorporation *Cannabis* derived botanical drug product alone or with the addition of other substances.

Unless otherwise indicated, the term "gel" relates to compositions that liquefy upon contact with the skin.

Unless otherwise indicated, the term "paste" relates to compositions where at least the three following agents—oil, water, and powder—are combined; an ointment in which a powder is suspended.

Unless otherwise indicated, the term "lotion" relates to a low- to medium-viscosity topical preparation intended for application to unbroken skin in contrast, creams and gels have higher viscosity. Lotions are applied to external skin with bare hands, a clean cloth, cotton wool or gauze. Many lotions, especially hand lotions and body lotions are formulated not as a medicine delivery system, but simply to smooth, re-hydrate, and soften the skin. These are particularly popular with the aging and aged demographic groups, and in the case of face usage, can also be classified as a cosmetic in many cases, and may contain fragrances.

Most lotions are oil-in-water emulsions using a substance such as cetyl alcohol to keep the emulsion together, but water-in-oil lotions are also formulated. The key components of a skin care lotion, cream or gel emulsion (that is mixtures of oil and water) are the aqueous and oil phases, an emulsifier to prevent separation of these two phases, and, if used, the drug substance or substances. Other ingredients are commonly added to lotions, such as fragrances, glycerol, petroleum jelly, dyes, preservatives, proteins and stabilizing agents. Lotions can be used for the delivery to the skin of medications such as: antibiotics; antiseptics; antifungals; corticosteroids; anti-acne agents; and soothing, smoothing, moisturizing or protective agents.

In some embodiments of the present invention, the same drug ingredient can be formulated into a lotion, cream and ointment. Creams are the most convenient of the three but are inappropriate for application to regions of hairy skin such as the scalp, while a lotion is less viscous and may be readily applied to these areas (many medicated shampoos are in fact lotions). Non-comedogenic lotions are recommended for use on acne prone skin.

In some embodiments of the present invention, formulations containing *Cannabis* derived botanical drug product include preparations where all or part of the oil component is hemp oil. These preparations may also comprise any of the other *Cannabis* derived botanical drug products to provide benefit inherent to these materials, such as antibiotics; antiseptics; antifungals; corticosteroids; anti-acne agents; and soothing, smoothing, moisturizing or protective agents.

In some embodiments, the topical formulations can be in the form of a nasal spray, which usually comprise decongestants and other medications to treat rhinitis, allergy, other conditions associated with swollen tissue and fluid secretion. Nasal sprays are usually applied directly to the nasal cavity. By applying them directly to the site of action, topical decongestants relieve nasal congestion while reducing the side effects associated with systemically-acting decongestants, such as high blood pressure. Topical decongestants are a common form of nasal relief, due to their quick effects which can clear the sinus in quickly.

In some embodiments, the topical formulations can be in the form of a soap, which are formulations that comprise a salt of a fatty acid. Soaps are mainly used as surfactants for washing, bathing, and cleaning, but they are also used in textile spinning and are important components of lubricants. Soaps for cleansing are usually obtained by treating vegetable or animal oils and fats with a strongly alkaline solution. Fats and oils are composed of triglycerides; three molecules of fatty acids are attached to a single molecule of glycerol. The alkaline solution, which is often called lye (although the term "lye soap" refers almost exclusively to soaps made with sodium hydroxide), is believed to promote a chemical reaction known as saponification. In saponification, the fats are first hydrolyzed into free fatty acids, which then combine with the alkali to form crude soap. Glycerol (glycerine) is usually liberated and is either left in or washed out and recovered as a useful byproduct, depending on the process employed.

In some embodiments, the topical formulations can be in the form of a shampoo, which is a hair care product used for the removal of oils, dirt, skin particles, dandruff, environmental pollutants and other contaminant particles that gradually build up in hair. A goal may be to remove the unwanted build-up without stripping out so much sebum as to make hair unmanageable.

Another embodiment of the present invention is a method of making the topical formulation in the form of a cream, which comprises (i) dispersing lake/powder into mineral oil or silicone oil to obtain an oil phase; (ii) dispersing an emulsifier, a thickener; and a stabilizer into water in a separate vessel to obtain an aqueous phase; (iii) blending the oil phase and the aqueous phase to form an emulsion; and (iv) dispersing an active ingredient such as a *Cannabis* derived botanical drug product into at least one of the oil phase, the aqueous phase, and the emulsion. In some embodiments, the method further comprises heating during at least one of (i) dispersing lake/powder into mineral oil or silicone oil to obtain an oil phase and (ii) dispersing an emulsifier, a thickener; and a stabilizer into water in a separate vessel to obtain an aqueous phase. Temperatures of this heating are not particularly limited, so long as the oil phase and the aqueous phase result from the dispersing.

Another embodiment of the present invention is a method of making the topical formulation in the form of a lotion, which comprises mixing an oil phase comprising hemp oil with an emulsifier and with an aqueous phase to form a mixture and heating said mixture at a temperature of from 45 and 85° C. to form an aqueous emulsion. Emulsifiers include, but are not limited to, cetyl alcohol, stearic acid, and a mixture thereof. The water phase comprises a stabilizing agent such as VEEGUM® or CARBOPOL®.

Another embodiment of the present invention is a method of making the topical formulation in the form of a shampoo, which comprises combining a surfactant, most often sodium lauryl sulfate and/or sodium laureth sulfate with a co-surfactant, most often cocamidopropyl betaine, in an aqueous phase and mixing the aqueous phase to form a thick, viscous liquid. Preferred methods further comprise adding other ingredients, such as salt (sodium chloride), a preservative, and fragrance, to the aqueous phase.

Another embodiment of the present invention is a method of treating a dermatological disease, which comprises applying a therapeutically effective amount of the topical formulation according to the present invention to skin affected with a dermatological disease. Non-limiting examples of targeted dermatological diseases include eczema, psoriasis, sunburn, contact dermatitis, poison ivy and conditions caused by other plant materials containing urushiol or related molecules, type 1 and type 2 herpes, insect bites, anal itching, vaginal itching, acne, warts and other acute and chronic dermatoses afflicting humans, and use as a topical analgesic for muscle and arthritic pain. Psoriasis is the preferred targeted dermatological disease.

Additionally, formulations can be tailored and used to treat veterinary dermatoses including seborrhea, keratinization, ichthyosis, sebaceous adenitis, among other hair and dermatological disease occurring in animals. Cosmetic formulations including lotions, creams, soaps, shampoos, lip balms are that are designed for moisturizing, anti-aging, anti-wrinkle, acne treatment, rough skin treatment, and dandruff.

Unless indicated otherwise, the term "therapeutically effective amount" is not particularly limited, so long as at least one of THC and CBD is present in an amount effective for treating the dermatological disease. Preferably, the therapeutically effective amount of at least one of THC and CBD is from 2 to 100 milligrams per kilogram, more preferably from 2 to 50 milligrams per kilogram, and more preferably from 2 to 25 milligrams per kilogram. The most preferred therapeutically effective amount of THC and/or CBD in the topical formulation according to the present invention is from 2 to 10 milligrams per kilogram. All rational numbers between the preceding minima and maxima are included in the ranges.

EXAMPLES

The following non-limiting examples are intended to illustrate the present invention.

Example 1

Moisturizing Lotion

A lotion is formulated by mixing an emulsifier with hemp oil itself or by mixing hemp oil and at least one other oil to produce an emulsion with water. An emulsifier such as cetyl alcohol or stearic acid was added to the oil phase. The water phase is prepared separately and contains stabilizing agents such as VEEGUM® or CARBOPOL®. The mixture is heated to between 45 and 85° C. and mix until a stable emulsion is formed.

Example 2

Moisturizing Lotion with CBD

A lotion is prepared as described in Example I. Another *Cannabis* derived Botanic drug product is added to either the water phase or the oil phase to achieve a CBD concentration of 2 mg per kilogram or more in the final product.

Example 3

Moisturizing Lotion with CBD

A *Cannabis* derived botanic drug Product is added to a commercially available lotion base to achieve a CBD concentration of 2 mg per kilogram or more in the final lotion.

Example 4

Moisturizing Lotion with THC

A lotion is prepared as described in Example 1. Another *Cannabis* derived botanic drug product is added to either the water phase or the oil phase to achieve a THC concentration of 2 mg per kilogram or more in the final product.

Example 5

Moisturizing Lotion with THC

A *Cannabis* derived botanic drug product is added to commercially available lotion base to achieve a THC concentration of 2 mg per kilogram or more in the final product.

Example 6

Multi-Action Lotion

A lotion is prepared as described in Example 1. Another *Cannabis* derived botanic drug product is added to either the water phase or the oil phase to achieve a CBD concentration of 2 mg per kilogram or more in the final product and the THC concentration of 2 mg per kilogram or more in the final product.

Example 7

Multi-Action Lotion

A *Cannabis* derived botanic drug product is added to commercially available lotion base to achieve a CBD concentration of 2 mg per kilogram or more in the final product and the THC concentration of 2 mg per kilogram or more in the final product.

Example 8

Anti-Pruritic Lotion

A lotion is prepared as in Example 4 or Example 5 above. Benzocaine is added to the preparation to enhance the anti-puritic properties of the product As noted above, lotions targeted to a wide variety of medicinal uses can be prepared using the described methodology and where appropriate the addition of other agents to the preparation may supplement the pharmacologic actions of the *Cannabis* derived botanical drug product. Options for preparation of lotions include formulations as described in Examples 2, 3, 4, 5, and 6 where no hemp oil is used.

Example 9

Anti-Inflammatory Cream

A cream is prepared as described above and *Cannabis* derived botanic drug product is added to achieve CBD and/or THC levels of greater than 2 mg/kg of final product.

Example 10

Feminine Hygene Cream

A cream is prepared as described in Example 9 with benzocaine and resorcinol incorporated in a therapeutically effective amount.

Example 11

Fortified Anti-Inflammatory Cream

A cream is formulated as in Example 9 with a therapeutically effective amount of hydrocortisone or any of the other steroid within Groups I to VII in the US classification system incorporated into the cream.

Example 12

Arthritis Cream

A cream is formulated as in Example 9 with a therapeutically effective amount of methyl salicylate and menthol incorporated into the cream.

Example 13

Fever Sore Ointment

A *Cannabis* derived botanical drug product is dispersed in O/W emulsion base (Hydrophilic Ointment) so that the concentration for both THC and CBD in the emulsion is greater than 2 mg/kg.

Example 14

Extra Strength Fever Sore Ointment

An ointment is prepared as described in Example 13 but includes the addition of dimethicone, camphor, menthol, and phenol in the ointment.

Example 15

Veterinary Liniment

A formulation is prepared that comprises hemp oil, alcohol, and an essential oil such a eucalyptus and menthol.

Example 16

Equine Liniment

A formulation as described Example 15 is prepared and also comprises witch hazel and *Cannabis* derived botanical drug product so that the concentration for both THC and CBD is greater than 2 mg/kg.

Example 17

Veterinary Herbal Tonic

An emulsion is prepared using hemp oil and stabilizing agents. *Cannabis* derived Botanic Drug Product is included in the emulsion to achieve THC and or CDD concentrations of more than 2 mg/kg.

Example 18

Nasal Spray

A *Cannabis* derived botanic drug substance is dispersed in a solution containing a combination of excipients which may include cellulose, glycerol, sodium citrate, citric acid monohydrate, polysorbate 80, benzalkonium chloride, purified water. The final product contains CBD and/or THC at concentrations of more than 2 mgc/kg. This solution is dispensed into containers that facilitate spraying an aerosol into the nasal cavity.

Example 19

*Cannabis* Herbal Soap

A soap is prepared by standard saponification of oils and fats that may include hemp oil. As the preparation is cooling *Cannabis* derived botanical drug product is added to the soap to achieve THC and or CDB concentrations of greater than 2 mg/kg.

Example 20

*Cannabis* Herbal Glycerin Soap

A *Cannabis* derived botanical drug product is formulated with commercially available glycerin soap base to achieve final CBD and/or THC concentrations of more than 2 mg/kg.

Example 21

*Cannabis* Herbal Shampoo

A *Cannabis* derived botanical drug product is formulated with commercially available Shampoo base to achieve final CBD and/or THC concentrations of more than 2 mg/kg. Essential oils and perfumes may be added.

Example 22

Lip Balm

A commercially available lip balm is supplemented with a *Cannabis* derived botanical drug product is added to achieve THC and or CDB concentrations of greater than 2 mg/kg.

Example 23

Sunscreen

A sunscreen formulation is prepared as a lotion described in Example 1, 2, 3, 4, or 5 above and comprises a sun-blocking agent as described in: Title 21—Food And Drugs; Chapter I—Food And Drug Administration; Department Of Health And Human Services Subchapter D—Drugs For Human Use; Part 352 Sunscreen Products for Over-The-Counter Use.

We claim:

1. A topical formulation consisting essentially of an extract of *cannabis sativa* or *cannabis* indicia and at least one component selected from the group consisting of capsaicin, benzocaine, lidocaine, camphor, benzoin resin, methylsalicilate, triethanolamine salicylate, hydrocortisone, and salicylic acid, present in an amount of at least 0.1 wt % in the topical formulation, wherein the concentration of tetrahydrocannabinol in the topical formulation is greater than 2 milligrams per kilogram in the topical formulation, said topical formulation obtained by dispersing the extract of *cannabis sativa* or *cannabis* indicia in a water-in-oil emulsion, an oil-in-water emulsion, a wax-in-oil base, or an oil-in-wax base consisting essentially of at least one component selected from the group consisting of capsaicin, benzocaine, lidocaine, camphor, benzoin resin, methylsalicilate, triethanolamine salicylate, hydrocortisone, and salicylic acid.

2. The topical formulation according to claim 1, wherein said component is capsaicin.

3. The topical formulation according to claim 1, wherein said component is benzocaine.

4. The topical formulation according to claim 1, wherein said component is lidocaine.

5. The topical formulation according to claim 1, wherein said component is camphor.

6. The topical formulation according to claim 1, wherein said component is benzoin resin.

7. The topical formulation according to claim 1, wherein said component is methylsalicilate.

8. The topical formulation according to claim 1, wherein said component is triethanolamine salicylate.

9. The topical formulation according to claim 1, wherein said component is hydrocortisone.

10. The topical formulation according to claim 1, wherein said component is salicylic acid.

11. A topical formulation consisting essentially of an extract of *cannabis sativa* or *cannabis* indicia and at least one component selected from the group consisting of capsaicin, benzocaine, lidocaine, camphor, benzoin resin, methylsalicilate, triethanolamine salicylate, hydrocortisone, and salicylic acid, present in an amount of at least 0.1 wt % in the topical formulation, wherein the concentration of cannabidiol in the topical formulation is greater than 2 milligrams per kilogram in the topical formulation, said topical formulation obtained by dispersing the extract of *cannabis sativa* or *cannabis* indicia in a water-in-oil emulsion, an oil-in-water emulsion, a wax-in-oil base, or an oil-in-wax base consisting essentially of at least one component selected from the group consisting of capsaicin, benzocaine, lidocaine, camphor, benzoin resin, methylsalicilate, triethanolamine salicylate, hydrocortisone, and salicylic acid.

12. The topical formulation according to claim 11, wherein said component is capsaicin.

13. The topical formulation according to claim 11, wherein said component is benzocaine.

14. The topical formulation according to claim 11, wherein said component is lidocaine.

15. The topical formulation according to claim 11, wherein said component is camphor.

16. The topical formulation according to claim 11, wherein said component is benzoin resin.

17. The topical formulation according to claim 11, wherein said component is methylsalicilate.

18. The topical formulation according to claim 11, wherein said component is triethanolamine salicylate.

19. The topical formulation according to claim 11, wherein said component is hydrocortisone.

20. The topical formulation according to claim 11, wherein said component is salicylic acid.

21. A topical formulation consisting essentially of an extract of *cannabis sativa* and *cannabis* indicia and at least one component selected from the group consisting of capsaicin, benzocaine, lidocaine, camphor, benzoin resin, methylsalicilate, triethanolamine salicylate, hydrocortisone, and salicylic acid, present in an amount of at least 0.1 wt % in the topical formulation, wherein the concentration of each of tetrahydrocannabinol and cannabidiol in the topical formulation is greater than 2 milligrams per kilogram in the topical formulation, said topical formulation obtained by dispersing the extract of *cannabis sativa* and *cannabis* indicia in a water-in-oil emulsion, an oil-in-water emulsion, a water in oil emulsion, wax in oil base, or an oil-in-wax base consisting essentially of at least one component selected from the group consisting of capsaicin, benzocaine, lidocaine, camphor, benzoin resin, methylsalicilate, triethanolamine salicylate, hydrocortisone, and salicylic acid.

22. The topical formulation according to claim 21, wherein said component is capsaicin.

23. The topical formulation according to claim 21, wherein said component is benzocaine.

24. The topical formulation according to claim 21, wherein said component is lidocaine.

25. The topical formulation according to claim 21, wherein said component is camphor.

26. The topical formulation according to claim 21, wherein said component is benzoin resin.

27. The topical formulation according to claim 21, wherein said component is methylsalicilate.

28. The topical formulation according to claim 21, wherein said component is triethanolamine salicylate.

29. The topical formulation according to claim 21, wherein said component is hydrocortisone.

30. The topical formulation according to claim 21, wherein said component is salicylic acid.

* * * * *